(12) United States Patent
Bui (10) Patent No.: US 10,199,940 B1
(45) Date of Patent: Feb. 5, 2019

(54) DIRECT CURRENT POWER DELIVERY SYSTEM

(71) Applicant: ENRG-dc, Inc., Orange, CA (US)

(72) Inventor: Duc P. Bui, Orange, CA (US)

(73) Assignee: ENRG-dc, Inc., Orange, CA (US)

( * ) Notice: Subject to any disclaimer, the term of this patent is extended or adjusted under 35 U.S.C. 154(b) by 0 days.

(21) Appl. No.: 15/936,961

(22) Filed: Mar. 27, 2018

Related U.S. Application Data (60) Provisional application No. 62/477,919, filed on Mar. 28, 2017.

(51) Int. Cl.
| | |
|---|---|
| *H02M 3/158* | (2006.01) |
| *H01R 31/06* | (2006.01) |
| *H01R 24/76* | (2011.01) |
| *H01R 25/00* | (2006.01) |
| *H01R 27/02* | (2006.01) |
| *H02J 7/00* | (2006.01) |
| *H02J 1/00* | (2006.01) |
| *A61B 5/022* | (2006.01) |

(52) U.S. Cl.
CPC .......... *H02M 3/1584* (2013.01); *H01R 24/76* (2013.01); *H01R 25/003* (2013.01); *H01R 25/006* (2013.01); *H01R 27/02* (2013.01); *H01R 31/065* (2013.01); *H02J 7/0027* (2013.01); *H02J 7/0055* (2013.01); *A61B 5/022* (2013.01); *H02J 2001/008* (2013.01)

(58) Field of Classification Search
CPC .. H02M 3/1582; H02M 3/1584; H01R 24/76; H01R 25/003; H01R 25/006; H01R 27/02; H01R 31/065; H02J 7/0027; H02J 7/0055; H02J 2001/008
See application file for complete search history.

(56) References Cited

U.S. PATENT DOCUMENTS

| | | | |
|---|---|---|---|
| 6,160,728 A | 12/2000 | Peterson et al. | |
| 8,212,406 B2 | 7/2012 | Pichkur | |
| 8,700,224 B2 * | 4/2014 | Mathiowetz | H02J 3/14 |
| | | | 700/295 |
| 9,263,183 B2 * | 2/2016 | Chapman | H02J 3/383 |
| 2005/0173989 A1 | 8/2005 | Wu | |
| 2006/0131961 A1 * | 6/2006 | Ishii | H02M 3/158 |
| | | | 307/31 |
| 2013/0015714 A1 | 1/2013 | Kwok | |

(Continued)

FOREIGN PATENT DOCUMENTS

| | | |
|---|---|---|
| CN | 203503916 U | 3/2014 |
| CN | 203537037 | 4/2014 |

(Continued)

OTHER PUBLICATIONS

Chauhan et al., "Voltage Standardization of DC Distribution System for Residential Buildings," Journal of Clean Energy Technologies, vol. 4(3):167-172 (May 2016).

*Primary Examiner* — Matthew Nguyen
(74) *Attorney, Agent, or Firm* — Knobbe Martens Olson & Bear LLP (57) ABSTRACT

Several example multi-DC voltage (MDC) boxes and associated power delivery systems are described herein. The MDC box can take a 24-60 VDC input (or other values) and can provide multiple DC output voltages for electronic devices and medical devices to plug-in directly without having a need for a bulky AC-DC power adapter.

10 Claims, 13 Drawing Sheets

(56) References Cited

U.S. PATENT DOCUMENTS

2015/0188406 A1* 7/2015 Nishi .................. H02M 3/1584
323/217
2017/0077709 A1 3/2017 Kim et al.

FOREIGN PATENT DOCUMENTS

| | | |
|---|---|---|
| JP | 2009146827 | 7/2009 |
| JP | 2010027249 | 2/2010 |
| JP | 2010067458 | 3/2010 |
| JP | 2013125642 | 6/2013 |

* cited by examiner

DIRECT CURRENT POWER DELIVERY SYSTEM

INCORPORATION BY REFERENCE TO ANY RELATED APPLICATIONS

Any and all applications, if any, for which a foreign or domestic priority claim is identified in the Application Data Sheet of the present application are hereby incorporated by reference under 37 CFR 1.57.

BACKGROUND

Mains electricity is the general-purpose alternating-current (AC) electric power supply. It is the typical form of electrical power that is delivered to homes and businesses, and it is the typical form of electrical power that consumers use when they plug kitchen appliances, televisions, and electric lamps into wall sockets.

SUMMARY OF EXAMPLE EMBODIMENTS

In certain embodiments, a power delivery device can include a power receptacle having a housing and a power conversion circuit disposed in the housing. The power conversion circuit can include a plurality of power conversion sub-circuits that can receive a first direct current (DC) voltage from an input electrical wire and that can convert the first direct current voltage to a plurality of second direct current voltages different from the first direct current voltage. The plurality of power conversion sub-circuits can each include a DC-DC buck circuit. A plurality of outlets can be coupled with the power conversion circuit. The plurality of outlets can supply the plurality of second direct current voltages to separate electronic devices upon connection of the separate electronic devices to the outlets.

For purposes of summarizing the disclosure, certain aspects, advantages and novel features are discussed herein. It is to be understood that not necessarily all such aspects, advantages or features will be embodied in any particular embodiment disclosed herein, and a myriad of combinations of such aspects, advantages, or features may be implemented.

BRIEF DESCRIPTION OF THE DRAWINGS

The following drawings and the associated descriptions are provided to illustrate embodiments of the present disclosure and do not limit the scope of the claims.

While the foregoing "Brief Description of the Drawings" references generally various embodiments of the disclosure, such embodiments are not mutually exclusive. Rather, a myriad of combinations of some or all of such embodiments may be implemented.

DETAILED DESCRIPTION

Introduction

Rising energy costs coupled with increasing needs for sustainability have led the construction industry to seek ways to reduce the overall energy use of a building while also helping to curb construction costs. As people become more dependent on electronics (smart phones, tablets, laptops, monitors, etc.) within the built environment, the number and density of DC powered devices increases. Each time an AC-DC (alternating current to direct current) conversion is made to power such devices, there is a discrete amount of power lost during the conversion. The net result is numerous small external power adapters operating within the same room creating clutter and a substantial amount of power loss. At the same time, a significant portion of electrical construction costs go toward branch circuiting (including 120 VAC power from circuit panels in the form of conduit and conductors or metal-clad cables) to distribute the 120 VAC power to receptacles where these electronics and their AC/DC converters may be plugged-in. The 120 VAC power distribution is labor intensive, costly and difficult to modify—often requiring approved plans and a licensed contractor to perform.

The power electrical distribution systems throughout the United States have been based on an AC (Alternating Current) system for nearly 130 years ever since it was invented by George Westinghouse in 1888. The power company generates AC power and delivers it to the consumers via high voltage power lines—transforming it down to as low as 120 VAC or 220 VAC for household, industrial, commercial and even medical building usage. Similar systems operate, often at slightly different voltages, in other countries.

Today, in a digital age, almost all the electronic devices and LED (light-emitting diode) lights or luminaires use DC (Direct Current) voltage power to operate, yet many electronic devices use an AC-DC power adapter or driver to convert from AC power to DC power in order to power up. As far as the inventor is aware, there is no product available on the market that takes a DC power input and provides multiple DC output voltages, so that consumers can plug their electronic devices directly into a DC power source without having to carry an AC-DC power adapter with them. There is a definite need for having a low voltage DC power distribution system and corresponding DC power outlets available for the usage of the electronics devices that are routinely used as a part of our daily activities.

Advantageously, in certain embodiments, an MDC (Multi-DC Voltages) box and associated power delivery system is described herein. In certain embodiments, the MDC box takes a 24-60 VDC input (or other values) and provides multiple DC output voltages for electronic devices to plug-in directly without having a need for a bulky AC-DC power adapter.

In certain embodiments, the MDC box provides three (3) USB outlets and two (2) high speed USB Type-C at 5 VDC, total of 5 A for iPhone/iPad™ charging or other Android™ Smart Phones/Tablets, one (1) outlet at 19.5 VDC-5 A for charging most of the laptop or notebook computers, one (1) outlet at 12-15 VDC-4 A for charging Microsoft Surface™ devices and one (1) outlet at 14-20 VDC-5 A to power a large 25"-32" LED screen. However, many other configurations are possible, including configurations with fewer or more outlets, including at different voltages than those listed herein. Multiple outlets with the same voltage may also be provided in a single MDC box.

This MDC box can significantly reduce the need for 120 VAC outlets mounted in the wall. There can therefore be a major change in the electrical design for buildings that no longer need 120 VAC power distribution everywhere, such as hospitals, thus reducing electrical installation costs. The bulk of electrical design/installations can be low voltage, 24-60 VDC power distribution to each and every room in the building. However, many other configurations are possible.

The DC input power to the MDC Box can also provide the same source of DC power to LED lights for the room, so the LED lights may no longer need 120V or 277V AC power input. Lighting control, or dimming, can be accomplished by use of a wireless device and/or Bluetooth technology via computer applications (such as Smartphone Apps) or using Cat 5 wiring for the wall switches and lighting control devices. This design concept can eliminate the need for AC line voltage to LED light fixtures, which can reduce cost as well as exposure of individuals and animals to electric shock from the AC electrical power.

Switching from AC to DC power distribution for electronic devices may help improve the building environment on multiple fronts. It may help reduce losses by (for example) consolidating AC-to-DC transformation to centralized devices capable of carrying larger overall loads and improving overall efficiency of the system. It may clean up cabling clutter by allowing electronic devices to be plugged into the wall/floor utilizing a single cord, which may eliminate adapters and power supplies. And it may also allow a larger portion of the electrical delivery system to reside in the low-voltage (LV) realm where an electrical raceway is not required by many electrical codes.

By distributing power at 24-60 VDC to devices in lieu of 120 VAC, the system described herein may lower the risk of electrical shock. They system may not require the additional physical protection of conduits or metal-clad raceway. This, in turn, can create a system that is quicker, easier, and less costly to install, that may be modular in nature, and that may ultimately be more flexible and field adjustable.

Example Benefits for using the MDC box and/or associated DC distribution system:

1. May need only one VDC input, but may provide single or multiple VDC outputs.
2. May be much safer for the consumer to use, because it can be low voltage of DC power. May reduce or eliminates potential electrical shock hazards caused by the AC power.
3. Power can be clean and constant, so no additional surge arrester and filter may be required as they are for AC power. Surge suppression may be included on the AC power at the service entrance or at the power distribution level.
4. Class 2 or 3 Low Voltage wiring, may not need conduit or race way, which may create faster installation and cheaper costs compared to 120 VAC outlet wiring.
5. Many city and state agencies currently do not require Low Voltage wiring design to be submitted for plan check, review and inspection; therefore, no plan check and no city inspection may be required, which may create reduced time frames during the design and installation of the system.
6. May eliminate the need for the AC-DC power adapter, which can reduce waste energy and electronics waste, which may create a better environment.
7. May reduce the need for typical 120 VAC receptacle outlets.
8. May be modular and flexible. Users can easily relocate and reconfigure room layouts with the furniture arrangement without requiring a licensed electrician.

The same design concept of the MDC box can also apply for in-floor or raised floor, for large open workstation spaces as well as installing the MDC box on the table top of the conference table or in a modular classroom setting.

Example DC Power Distribution

Although installing the MDC box in lieu of the typical 120 VAC outlet can be a beneficial concept, at the branch circuiting level, large equipment such as air conditioning units and large motors currently still require AC power. The utility companies will likely continue to provide power to buildings with AC power for some time. The MDC box uses DC input power, so there may be a need for converting AC power to DC power ahead of the MDC box. For example, as a part of the electrical system design for the MDC box, an AC/DC electrical panel may be provided elsewhere in the building. The AC/DC electrical panel can be located in the electrical room of a building, providing AC power to selected equipment and convenience receptacles while providing DC power (e.g., 24-60 VDC) to the MDC boxes and/or LED light fixtures. The plenum- or non-plenum-rated low voltage cables that run from the DC panel to the MDC boxes can be installed within raised floor or hang on J-hook overhead in the ceiling space, although other installation solutions and conduit types may be used.

Solar power is typically produced at nominal output voltages of 12, 18 and 24 volts DC then stepped up to around 400-500 VDC for long distance distribution using small conductors. Regardless of the voltage output of solar panels, typically they output DC voltage. The DC power source may distribute DC power to a DC electrical panel, which can in turn deliver DC power to the MDC boxes without having to convert from AC to DC as is typically needed to be done today, saving power and electrical complexity.

The proposed DC voltage to be distributed to the MDC box is 48-60 volts in certain embodiments, so Class 2 or 3 low voltage wiring is allowed to be used without conduit with a limit up to 250 VA per circuit based on National Electrical Code (NEC) 11(b) Chapter 9. Other voltage levels may be used in other MDC embodiments.

MDC Box Design

An example MDC box is designed to receive a single source of 48-60 VDC power. Then, using a voltage conversion component, such as a DC-DC Buck component, the MDC box can reduce (or increase) the DC voltage and provide single or multiple DC output voltages. In lieu of using DC-DC Buck to step down the voltage (which does not typically employ a transformer), other example alternatives for reducing the voltage include using a step-down transformer(s) or using a flyback converter (for example, a single transistor driver). Many other configurations are possible.

The MDC box may have one (or optionally more) DC input(s) and provides any number of DC outputs. In one example implementation, the MDC box outputs three (3) USB outlets and two (2) high speed USB Type-C outlets at 5 VDC, total of 5 A for iPhone/iPad™ charging or other Android™ Smart Phones/Tablets, one (1) outlet at 19.5 VDC-5 A for charging most of the laptop or notebook computers, one (1) outlet at 12-15 VDC-4 A for charging Microsoft Surface™ devices and one (1) outlet at 14-20 VDC-5 A to power a large 25"-32" LED screen. Many other configurations are possible. Besides the USB Ports, the DC Power receptacles on the box can be designed with different sizes for each discrete DC voltage to prevent the user from plugging their electronics devices into the wrong voltage.

Example MDC Boxes and Circuits

Figure 1:
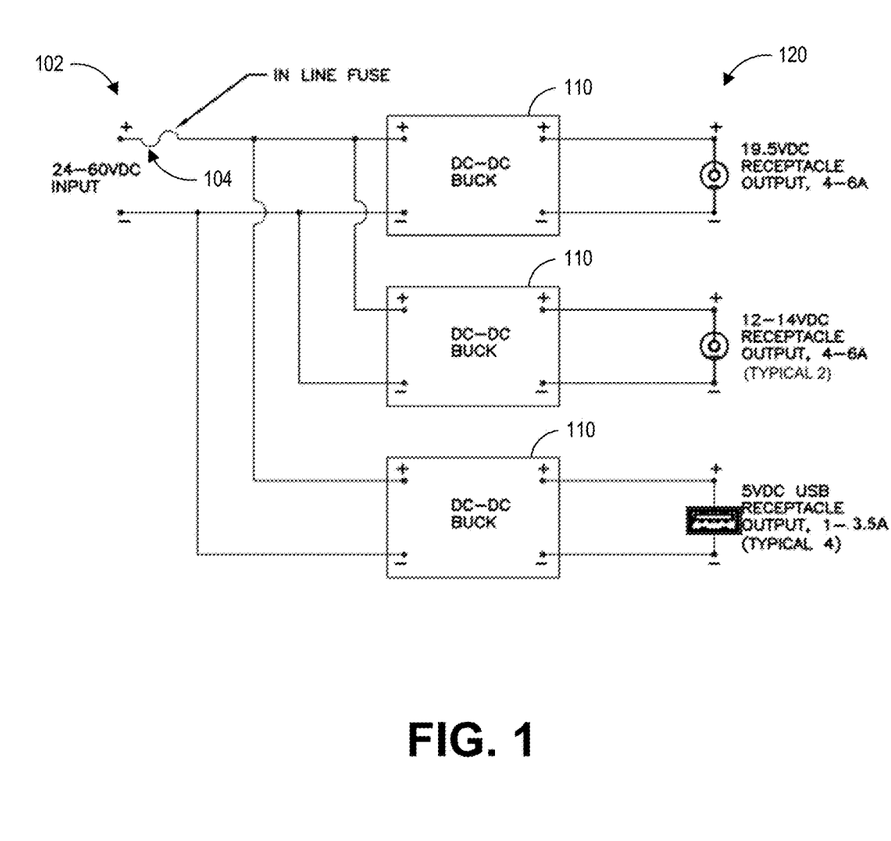
FIG. 1 depicts a block diagram showing an example circuit for a single DC Volt input buck to multiple step-down DC Volt outputs.

FIG. 1 depicts a block diagram showing an example power conversion circuit 100 for a single DC Volt input buck to multiple step-down DC Volt outputs. The example circuit 100 shown can be implemented in any of the MDC boxes described herein. The circuit 100 receives an input 102. The input 102 is between 24 and 60 VDC in the depicted embodiment. Other values are possible. An in-line fuse 104 is provided for over-current protection.

The input 102 may be received from an AC to DC converter, in, for example, an electrical room of the building separate from the power conversion circuit 100. The input 102 is shown being supplied to a plurality of DC-DC buck converters 110. The buck converters 110 are examples of power conversion sub-circuits of the power conversion circuit 100. Other example power conversion sub-circuits include step-down transformer(s) and flyback converters, as described above. Although three buck converters 110 are shown in the depicted embodiment, any number of buck converters 110 may be provided in other embodiments.

Each of the buck converters 110 provides an output 120. The three outputs 120 shown are each a different voltages to enable connection of different devices to the MDC box. Each of the outputs 120 may be provided as an outlet or as the receptacle output from the MDC box.

Figure 2A:
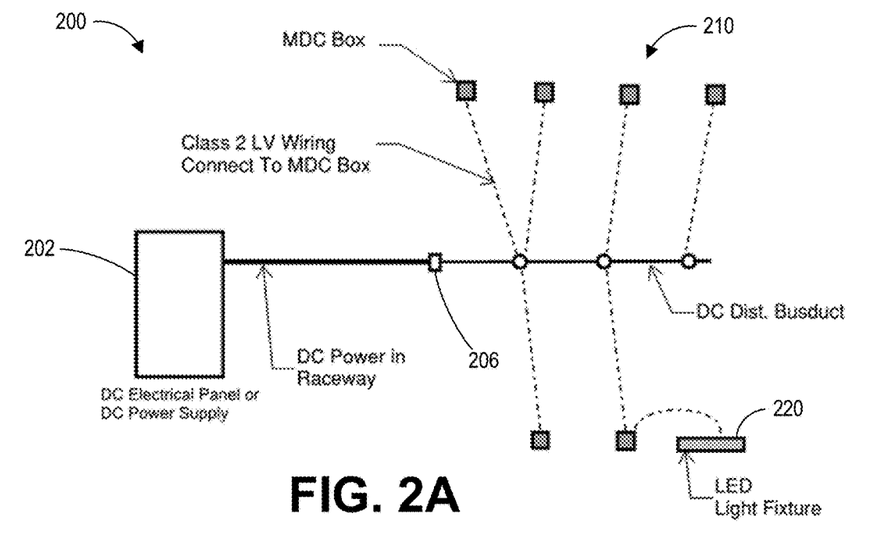
FIGS. 2A and 2B depict example DC power distribution systems for electrical power in a building.
Figure 2B:
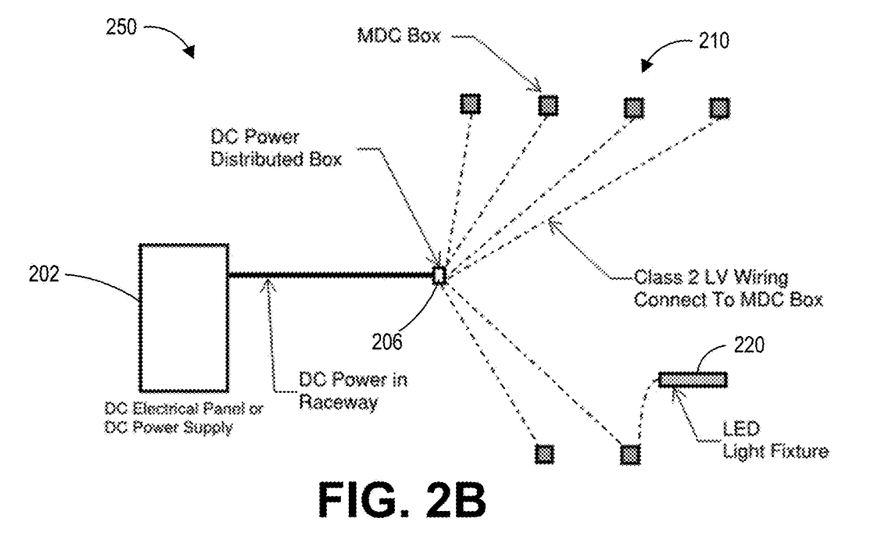

FIGS. 2A and 2B depict example DC power distribution systems 200, 250 for electrical power in a building. Each of the example power distribution systems 200, 250 shown can be implemented in a single building (such as the hospital) or through a plurality of buildings. Each example system 200, 250 shown includes a DC electrical panel or DC power supply 202. This power supply 202 receives AC power and/or DC power and outputs DC power. The AC power may come from an electrical utility company, whereas the DC power input may come from the solar panel or battery storage.

The power supply 202 outputs DC power, which may be in a raceway or other conduit, and which may be supplied to a DC power distribution box 206. The DC power distribution box 206 can distribute power to MDC boxes 210 directly (as in system 250) or indirectly through a DC distribution bus duct (as in the system 200). At least some of the MDC boxes 210 may be connected to LED light fixtures 220, while others may act as traditional outlets for DC-powered devices.

Figure 3A:
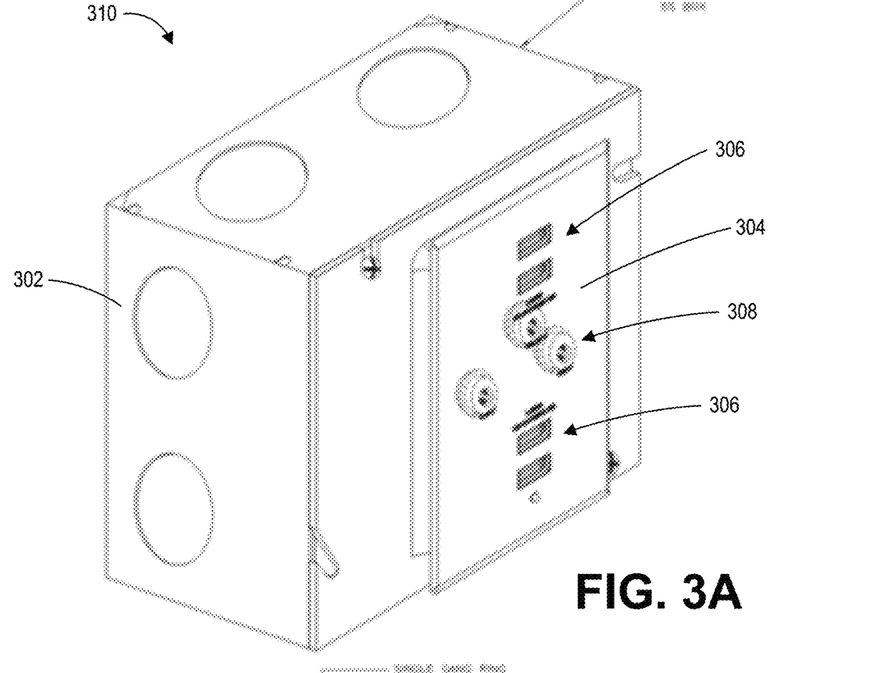
FIGS. 3A through 3C depict an embodiment of an MDC (Multiple DC Voltages) box and associated example face plate.
Figure 3B:
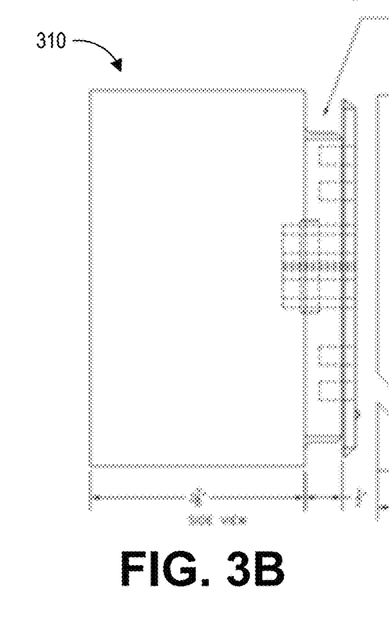
Figure 3C:
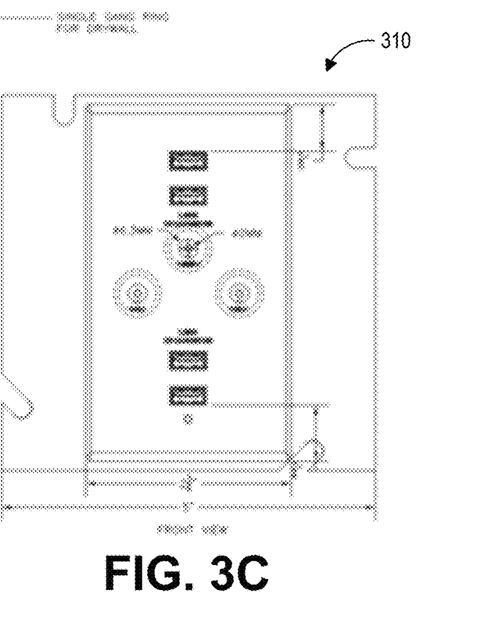

FIGS. 3A through 3B depict an embodiment of an MDC box 310 and associated example face plate 304. The example MDC box 310 is shown at three angles: a perspective angle in FIG. 3A, a side view angle in FIG. 3B, and a front view angle in FIG. 3C. The MDC box 310 includes an electrical box 302 and a faceplate 304. The electrical box 302 can contain the DC-DC power conversion circuit, such as the power conversion circuit 100 of FIG. 1 or the like. The faceplate 304 provides access to the outputs or outlets of the power conversion circuit. The example outlets shown include USB outlets 306 and circular power outlets 308, which may be suitable for connecting to laptop power adapters or other devices. The circular power outlets 308 each output a different voltage or the same voltage.

Figure 4A:
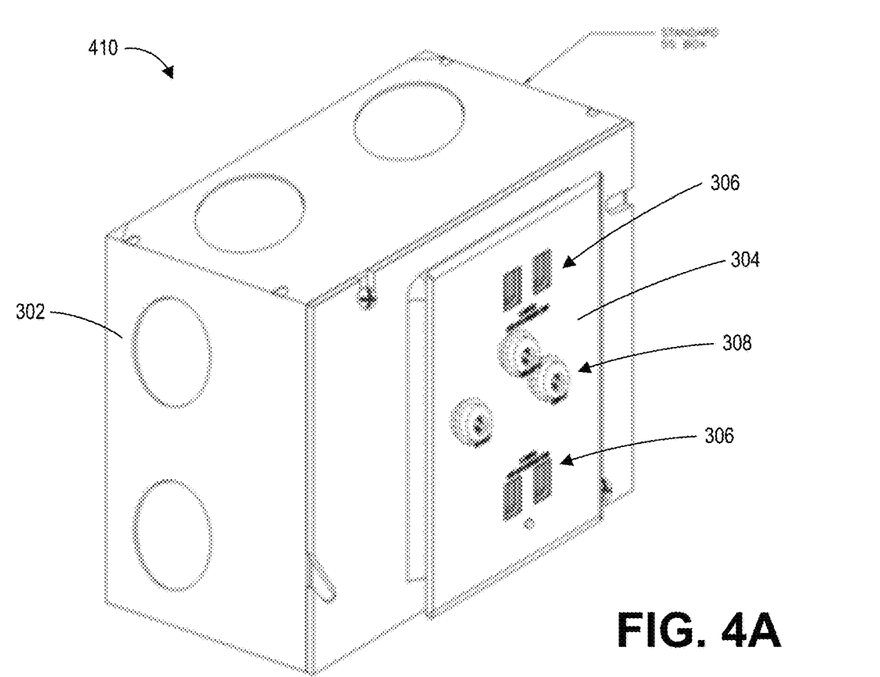
FIGS. 4A through 4C depict another embodiment of an MDC box and associated example face plate.
Figures 4B, 4C:
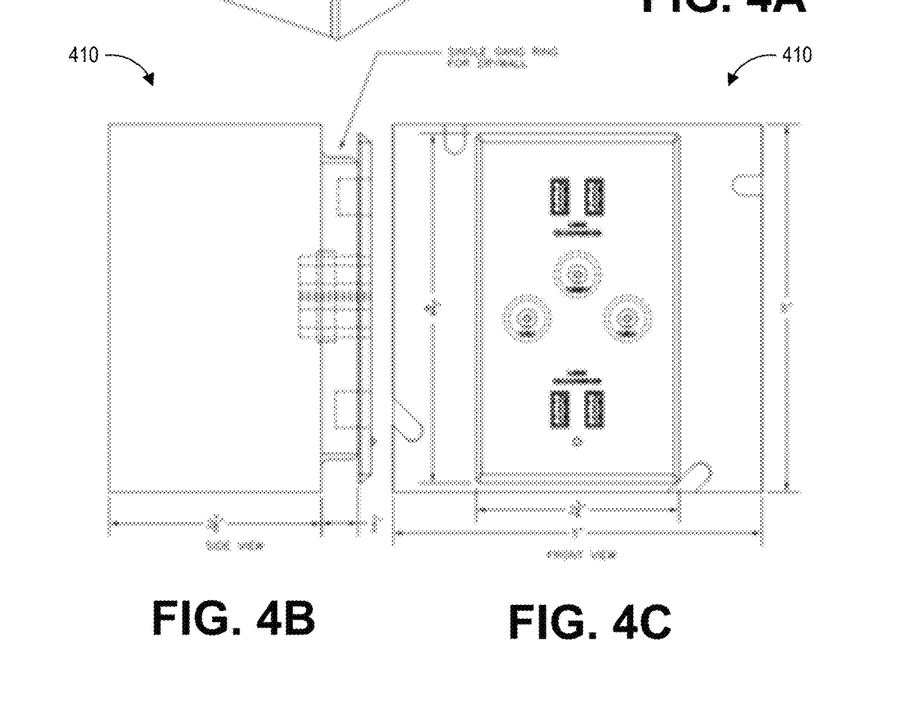

FIGS. 4A through 4C depict another embodiment of an MDC box and associated example face plate. The example MDC box 410 is shown at three angles: a perspective angle in FIG. 4A, a side view angle in FIG. 4B, and a front view angle in FIG. 4C. The MDC box 410 is similar to the MDC box 310, except that the USB outlets 306 are oriented vertically instead of horizontally, as in the MDC box 310.

Figure 5A:
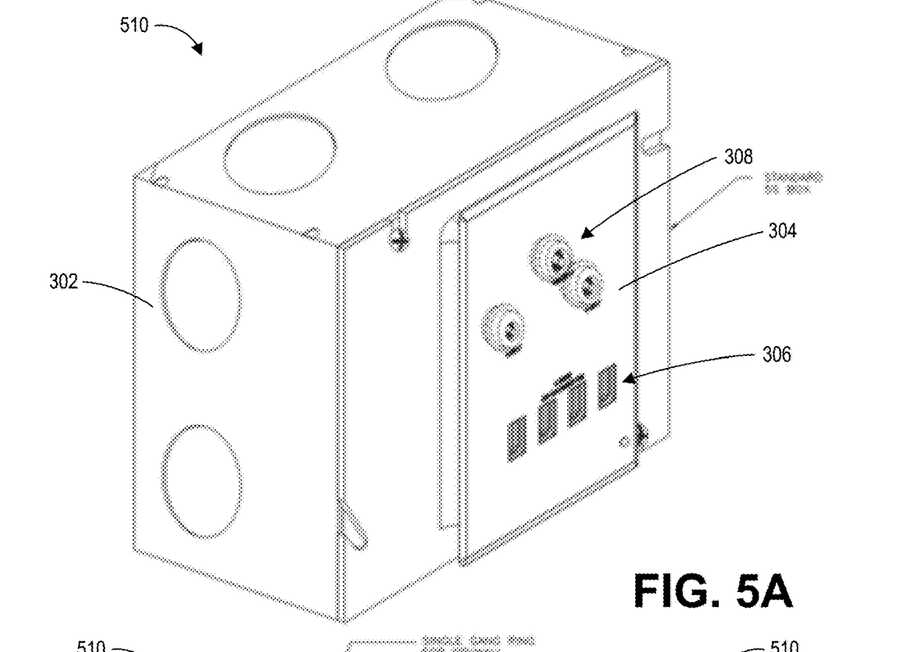
FIGS. 5A through 5C depict another embodiment of an MDC box and associated example face plate.
Figures 5B, 5C:
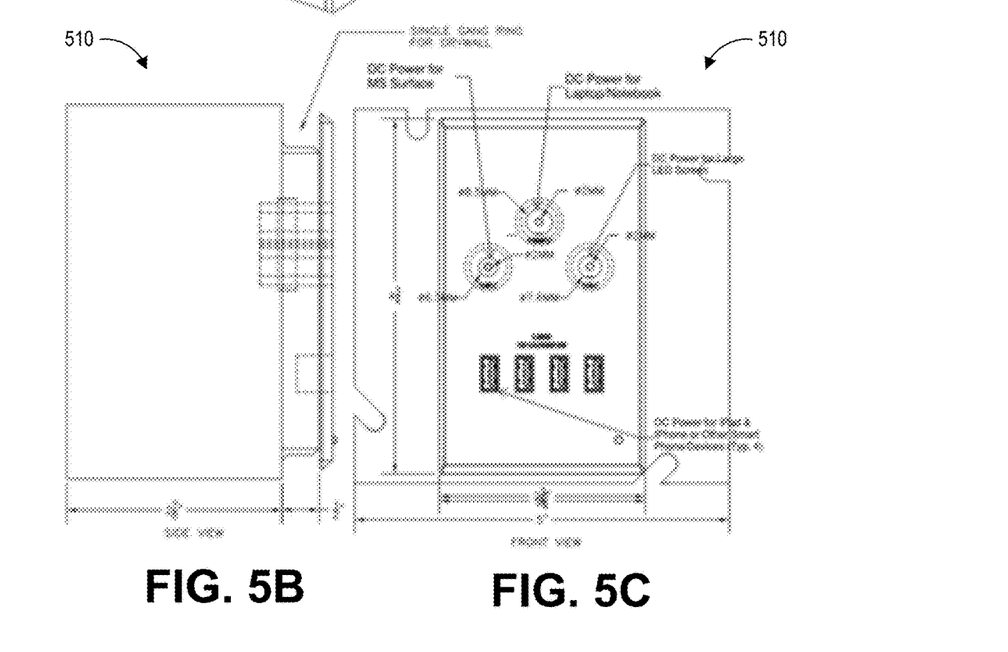

FIGS. 5A through 5C depict another embodiment of an MDC box and associated example face plate. The example MDC box 510 is shown at three angles: a perspective angle in FIG. 5A, a side view angle in FIG. 4B, and a front view angle in FIG. 4C. The MDC box 510 is similar to the MDC box 410 except that all four USB outlets 306 are grouped together below the circular power outlets 308. In contrast in the MDC box 410 (and 310), two of the USB outlets 306 are located above the circular power outlets 308 and the other two USB outlets 306 are located below the circular power outlets 308.

Figure 6A:
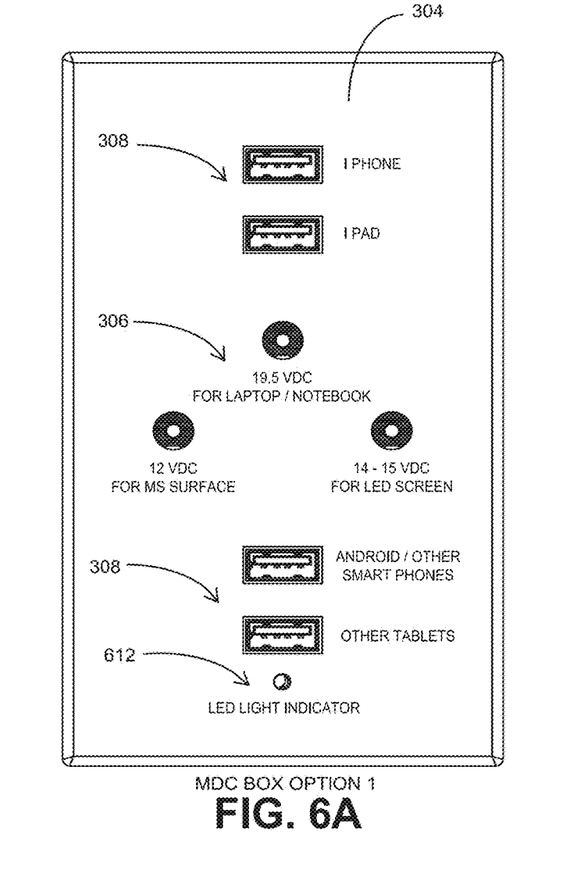
FIGS. 6A and 6B depict example wall-mounted MDC box faceplates.
Figure 6B:
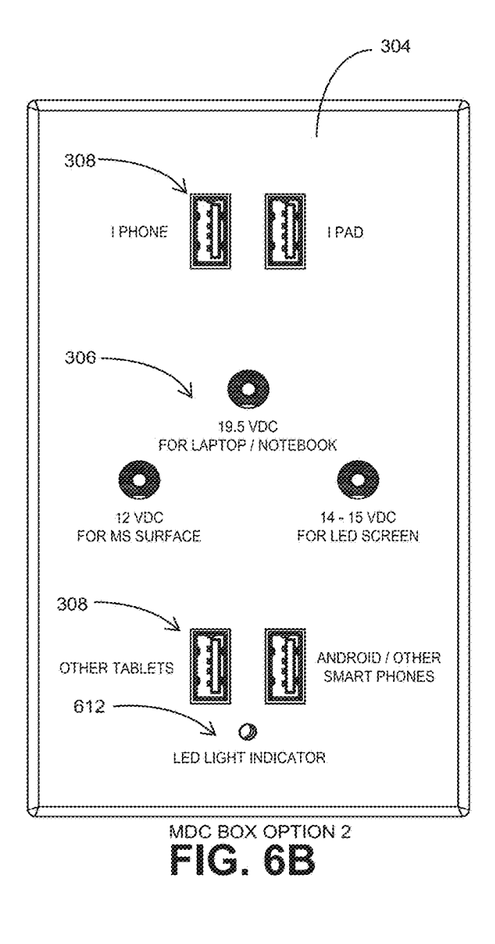

FIGS. 6A and 6B depict example wall-mounted MDC box faceplates 304. The faceplate 304 of FIG. 6A is similar to the faceplate 304 of FIGS. 3A-3C, while the faceplate 304 of FIG. 6B is similar to the faceplate 304 of FIGS. 4A-4C. In addition, each faceplate has example labels to show the types of devices (along with some voltages) that can be connected to the various outlets or ports shown. For example, some of the USB ports are labeled as iPhone™, iPad™, Android™ phones/other smart phones, and other tablets. The circular power outlets 306 are labeled 19.5 VDC for laptop/notebook, 12-15 VDC for MS Surface™, and 14-15 VDC for LED screen. These labels are optional and may be omitted or altered (for example, to show voltage and/or amperage output) in some embodiments. Moreover, an LED indicator light 612 is provided. LED light can be used for a variety of purposes. For example, the LED light can turn red when the MDC is over load (e.g., as measured by a current-sensing circuit in the MDC box). The LED light can be green when the MDC box is within a safe operating load.

Figure 7A:
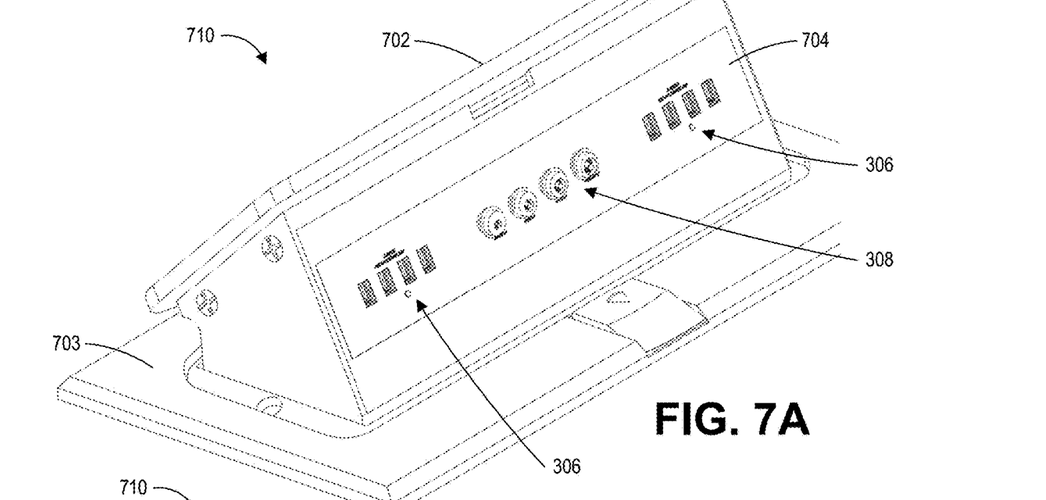
FIGS. 7A and 7B depict an embodiment of an MDC box mounted on a table top.
Figure 7B:
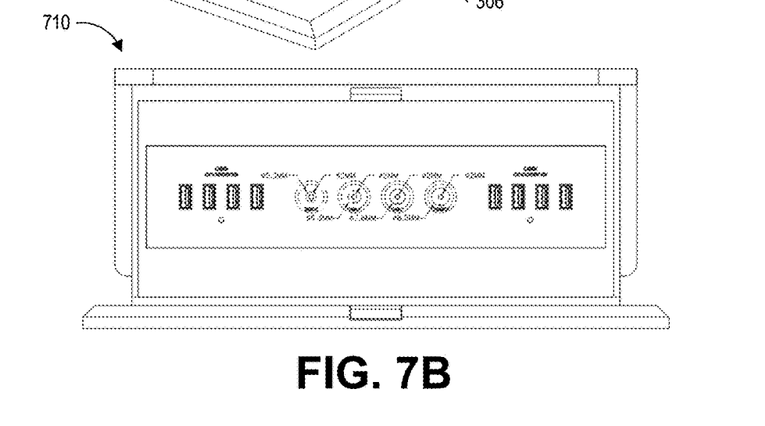

FIGS. 7A and 7B depict an embodiment of an MDC box 710 mounted on a table top. The MDC box 710 may be used, for example, in a conference room table. The MDC box 710 includes a box 702 that can be pushed downward to be flush or approximately flush with a base 703, which may be installed in or on the surface of a table. Like the previously described MDC boxes, the MDC box 710 includes USB ports 306 and circular power ports 308 installed in a faceplate 704.

Figure 8A:
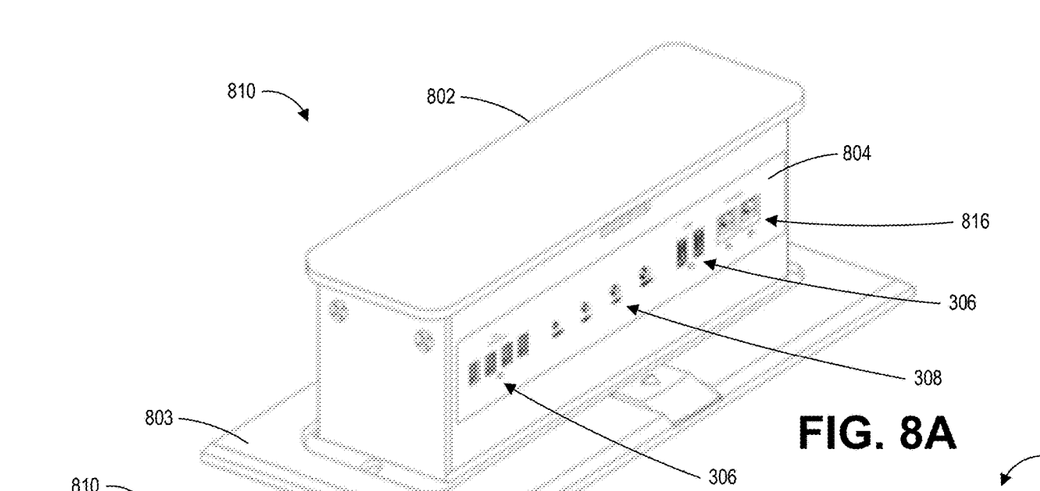
FIGS. 8A through 8C depict another embodiment of an MDC box mounted on a table top.
Figure 8B:
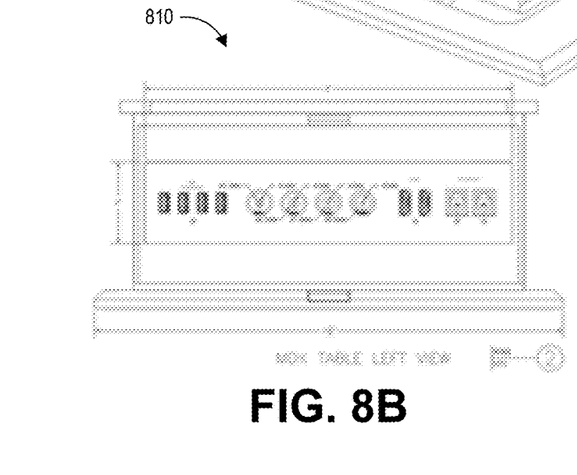
Figure 8C:
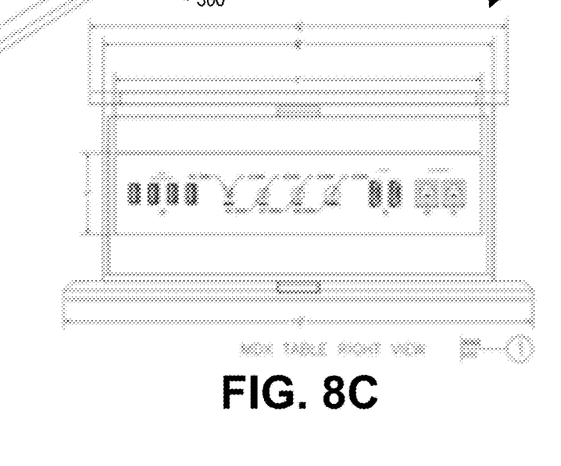

FIGS. 8A through 8C depict another embodiment of an MDC box mounted on a table top. The example MDC box 810 is shown in three views: a perspective view in FIG. 8A, a left side view angle in FIG. 8B, and a right side angle in FIG. 8C. The MDC box 810 may also be used, for example, in a conference room table. The MDC box 810 includes a box 802 that can be pushed downward to be flush or approximately flush with a base 803, which may be installed in or on the surface of a table. Like the previously described MDC boxes, the MDC box 810 includes USB ports 306 and circular power ports 308 installed in a faceplate 804. In addition, the MDC box 810 includes ethernet ports 816.

Figure 9A:
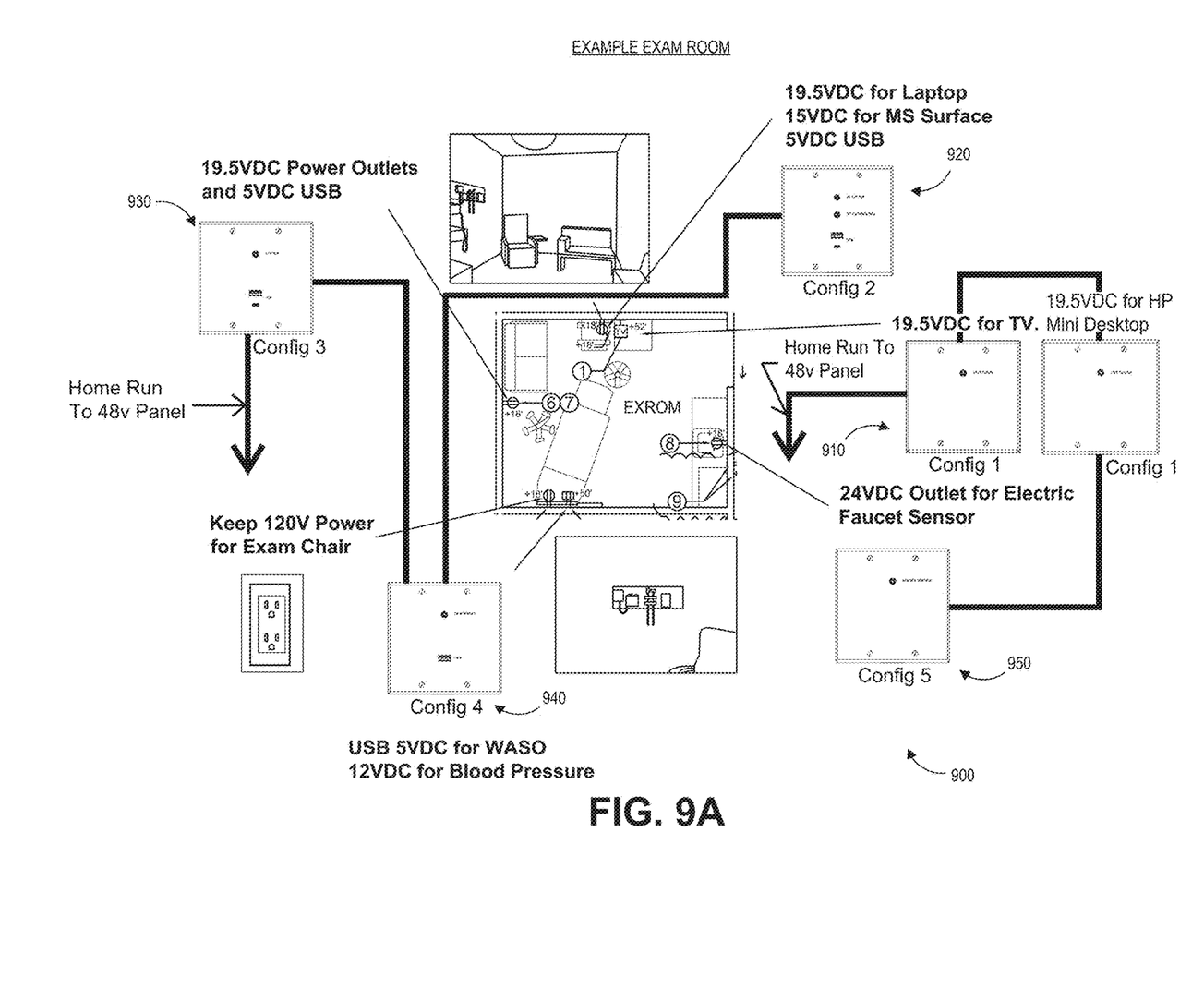
FIGS. 9A through 9E depict example MDC box scenarios for a clinical facility, such as a hospital or doctor's office.

FIGS. 9A through 9E depict example MDC box scenarios for a clinical facility, such as a hospital or doctor's office. FIG. 9A, for example, depicts an example MDC box scenario 900 in an example hospital exam room. FIG. 9A includes a floorplan of an example hospital exam room in the center, surrounded by images of example MDC box power outlets for various aspects of the room. Outlets 920, 930, and 940 are connected together on one circuit, while outlets 910 and 950 are connected together on another, different circuit. These outlet boxes can be provided with unique cable connectors for the cables connection as a plug-and-play concept. An AC 120V outlet is also shown being used in this room for powering the examination chair or table and is optional in some embodiments. The example outlets shown include outputs for USB, laptops, 12-15 VDC blood pressure, 5 VDC for WASO (example ophthalmoscope), 24 VDC for an electric faucet sensor, 19.5 VDC for a TV, and a 48 VDC for LED ceiling light fixture.

Figure 9B:
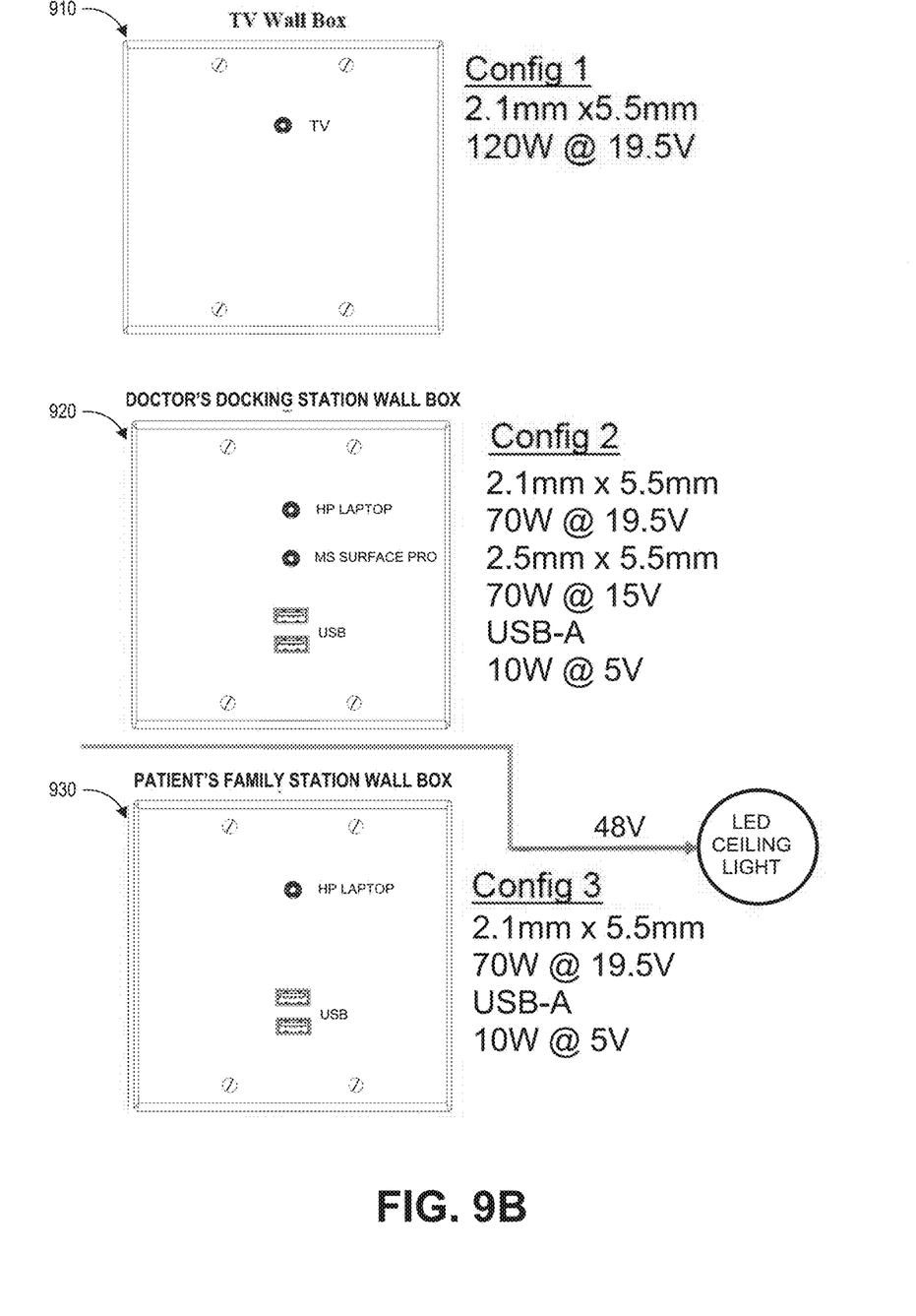

FIG. 9B depicts the example outlet covers 910, 920, and 930 from FIG. 9A in more detail, including a TV wall (MDC) box, a doctor's station wall (MDC) box, and a patient's family station wall (MDC) box (for patient person use). Although some of the ports are labeled with specific laptop names, these are just examples, and any laptop that has the matching voltage to the voltage output can connect to these outlets. Any suitable voltage for powering any suitable electronic device (such as laptops, tablets, e-readers, smartphones, etc.) can be provided in other embodiments.

Figure 9C:
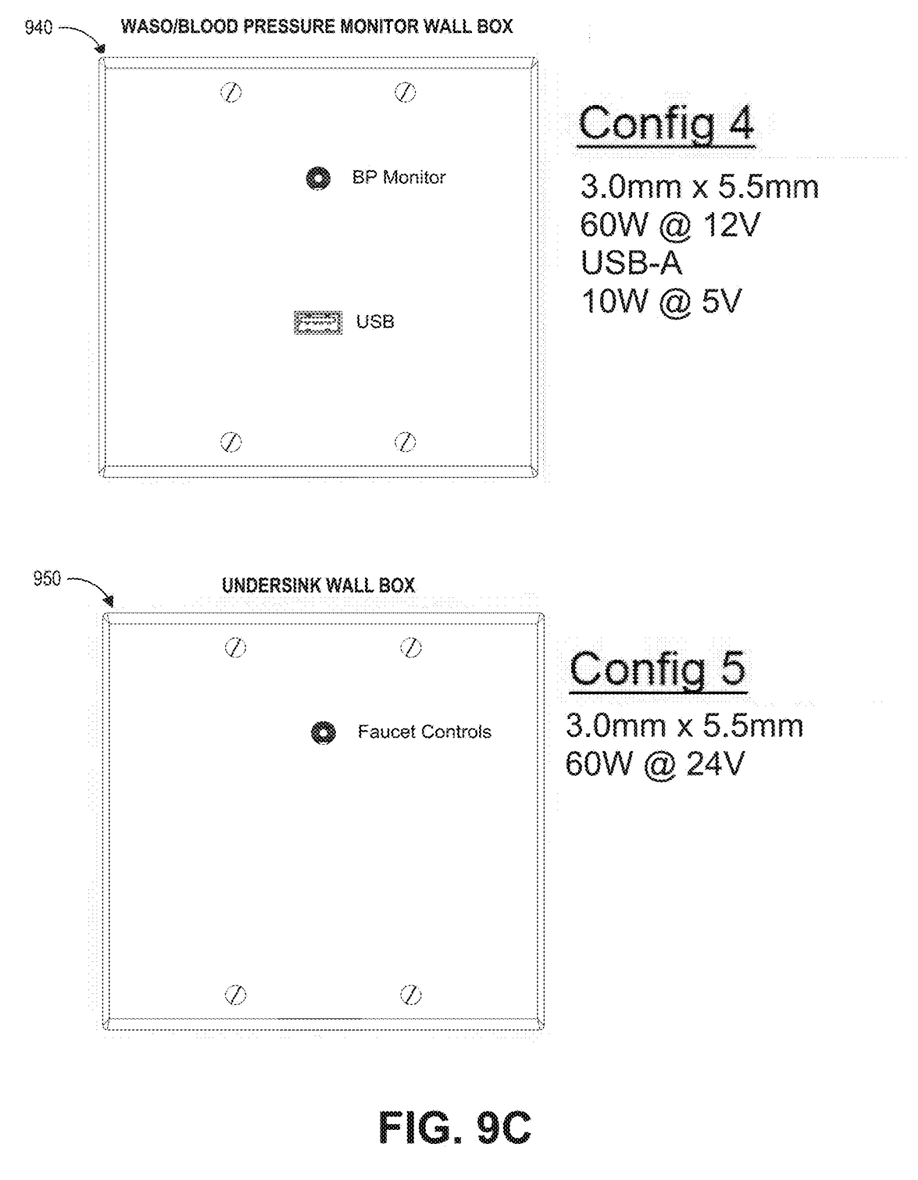
Figure 9D:
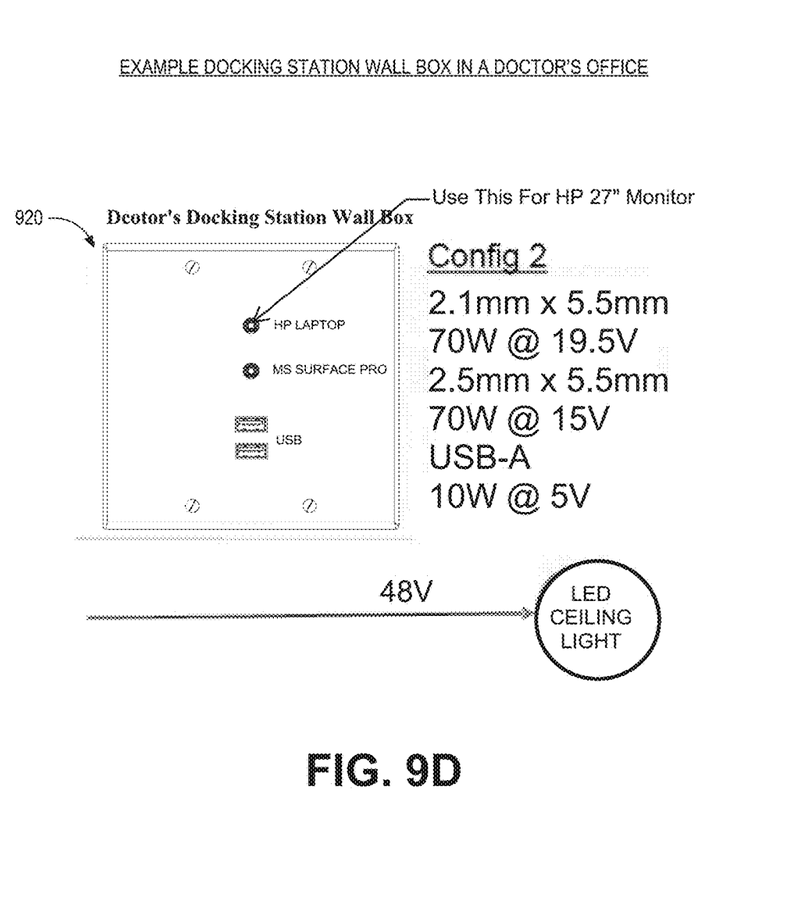
Figure 9E:
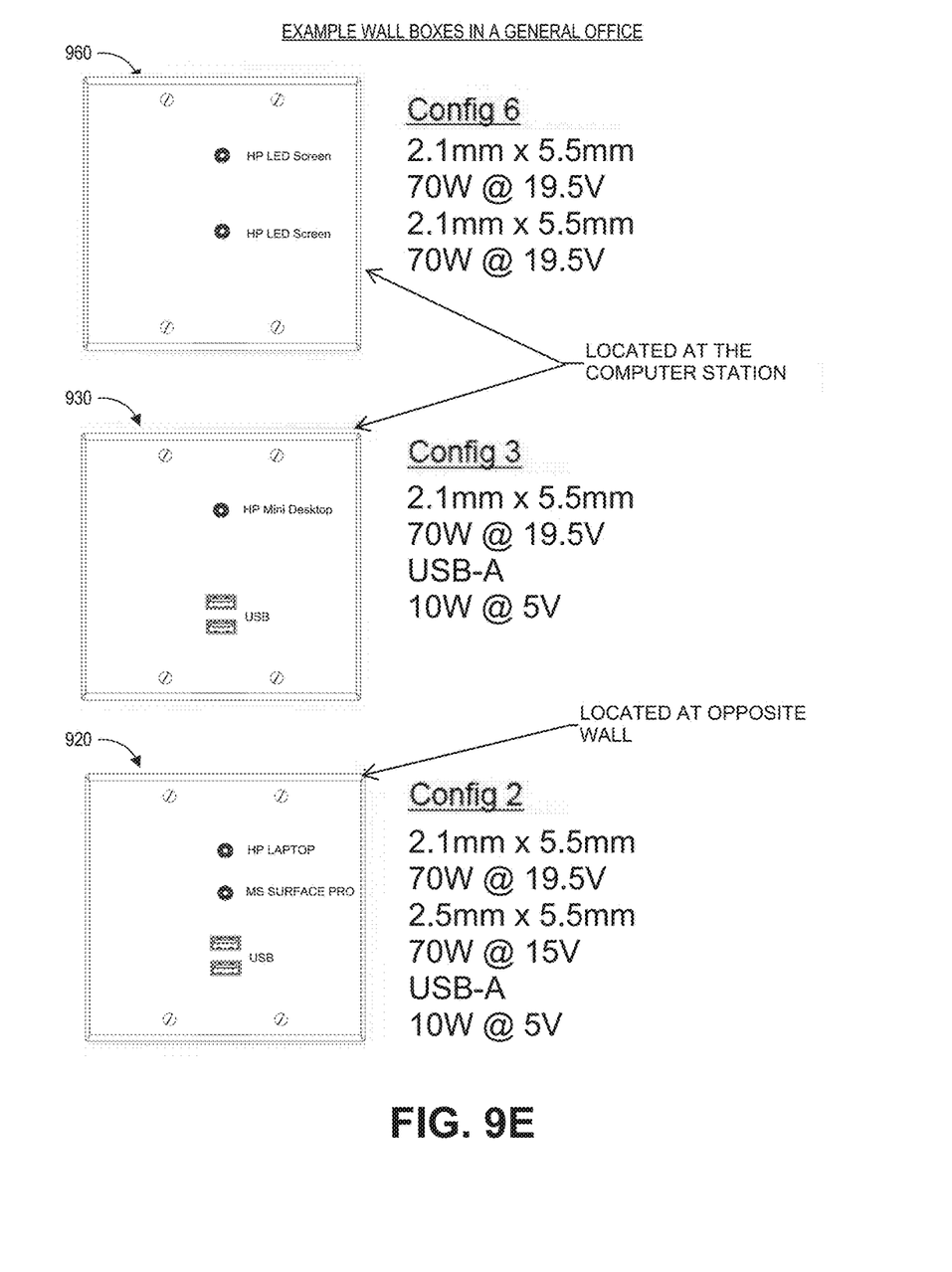

FIG. 9C depicts the example outlet covers 940 and 950 from FIG. 9A in more detail. These include outlet covers for a WASO/blood pressure monitor wall (MDC) box as well as an undersink (faucet) wall (MDC) box. FIG. 9D depicts the example wall (MDC) box 920 for use in a doctor's office. FIG. 9E depicts additional example wall (MDC) boxes 920, 930, 960 (for LED screens) for use in a general clinical office.

It should be understood that in various other implementations, any of the MDC boxes described herein could be varied to include fewer or more ports or outlets, as well as optionally different ports or outlets than the ones described herein.

Terminology

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Unless the context clearly requires otherwise, throughout the description and the claims, the words "comprise," "comprising," "include," "including," "having," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or" in reference to a list of two or more items, covers all of the following interpretations of the word: any one of the items in the list, all of the items in the list, and any combination of the items in the list. Likewise the term "and/or" in reference to a list of two or more items, covers all of the following interpretations of the word: any one of the items in the list, all of the items in the list, and any combination of the items in the list.

Depending on the embodiment, certain operations, acts, events, or functions of any of the algorithms described herein can be performed in a different sequence, can be added, merged, or left out altogether (e.g., not all are necessary for the practice of the algorithms). Moreover, in certain embodiments, operations, acts, functions, or events can be performed concurrently, e.g., through multi-threaded processing, interrupt processing, or multiple processors or processor cores or on other parallel architectures, rather than sequentially.

Any patents and applications and other references noted above, including any that may be listed in accompanying filing papers, are incorporated herein by reference. Aspects of the inventions can be modified, if necessary, to employ the systems, functions, and concepts of the various references described above to provide yet further implementations of the inventions.

These and other changes can be made to the inventions in light of the above Detailed Description. While the above description describes certain examples of the inventions disclosed herein, and describes the best mode contemplated, no matter how detailed the above appears in text, the inventions can be practiced in many ways. Details of the system may vary considerably in its specific implementation, while still being encompassed by the inventions disclosed herein. As noted above, particular terminology used when describing certain features or aspects of the inventions should not be taken to imply that the terminology is being redefined herein to be restricted to any specific characteristics, features, or aspects of the inventions with which that terminology is associated.

Any claims intended to be treated under 35 U.S.C. § 112(f) will begin with the words "means for", but use of the term "for" in any other context is not intended to invoke treatment under 35 U.S.C. § 112(f). Accordingly, the applicant reserves the right to pursue additional claims after filing this application, in either this application or in a continuing application.

What is claimed is:

1. A power delivery device comprising:
    a power receptacle comprising a housing;
    a power conversion circuit disposed in the housing, the power conversion circuit comprising a plurality of power conversion sub-circuits configured to receive a first direct current (DC) voltage from an input electrical wire and to convert the first direct current voltage to a plurality of second direct current voltages different from the first direct current voltage, wherein the plurality of power conversion sub-circuits each comprise a DC-DC buck circuit; and
    a plurality of outlets coupled with the power conversion circuit, the plurality of outlets configured to supply the plurality of second direct current voltages to separate electronic devices upon connection of the separate electronic devices to the outlets.

2. The power delivery device of claim 1, wherein the outlets comprise one or more of the following: a universal serial bus (USB) outlet, a laptop power outlet, a tablet power outlet, a monitor power outlet, a light emitting diode (LED) power outlet, and a smartphone power outlet.

3. The power delivery device of claim 1, further comprising an output to a light emitting diode (LED) power outlet.

4. The power delivery device of claim 1, wherein the first direct current voltage has a voltage between about 24 volts and 60 volts.

5. The power delivery device of claim 4, wherein the first direct current voltage has a voltage of 48 volts.

6. The power delivery device of claim 1, wherein the first direct current voltage is received directly from a solar panel.

7. The power delivery device of claim 1, wherein the first direct current voltage is received from an alternating-current to direct current (AC-DC) converter located separately from the power delivery device.

8. The power delivery device of claim 1, in combination with a plurality of other power delivery devices to form a plurality of DC-DC outlets for a hospital exam room.

9. The power delivery device of claim 8, wherein power delivery device and the plurality of other power delivery devices comprise a plurality of DC circuits separate from any AC circuits, except optionally for sharing a common ground line, in the hospital exam room.

10. The power delivery device of claim 9, wherein the plurality of DC circuits comprise a first circuit having at least one USB outlet, at least one 12-15 VDC outlet useable for a blood pressure device or an ophthalmoscope, and at least one 19.5 VDC outlet.

\* \* \* \* \*